United States Patent
Lao et al.

(10) Patent No.: US 8,765,988 B2
(45) Date of Patent: Jul. 1, 2014

(54) LYCOPENE INTERMEDIATE 1, 3, 6, 10-TETRA-DOUBLE BOND PENTADEC-CARBON PHOSPHONATE AS WELL AS PREPARATION METHOD AND USE THEREOF

(76) Inventors: Xuejun Lao, Zhejiang (CN); Runpu Shen, Zhejiang (CN); Weidong Ye, Zhejiang (CN); Xiaohua Song, Zhejiang (CN); Luo Liu, Zhejiang (CN); Chunlei Wu, Zhejiang (CN); Yibin Wu, Zhejiang (CN); Liujiang Hu, Zhejiang (CN)

( * ) Notice: Subject to any disclaimer, the term of this patent is extended or adjusted under 35 U.S.C. 154(b) by 0 days.

(21) Appl. No.: 13/583,635

(22) PCT Filed: Mar. 9, 2011

(86) PCT No.: PCT/CN2011/071657
§ 371 (c)(1),
(2), (4) Date: Sep. 9, 2012

(87) PCT Pub. No.: WO2011/110091
PCT Pub. Date: Sep. 15, 2011

(65) Prior Publication Data
US 2012/0330048 A1    Dec. 27, 2012

(30) Foreign Application Priority Data
Mar. 9, 2010   (CN) .......................... 2010 1 0120583

(51) Int. Cl.
*C07F 9/40*   (2006.01)

(52) U.S. Cl.
USPC .......................................................... 558/217

(58) Field of Classification Search
USPC ............................................................ 558/217
See application file for complete search history.

(56) References Cited

U.S. PATENT DOCUMENTS 5,973,179 A * 10/1999 Babler et al. .................... 558/83

* cited by examiner

*Primary Examiner* — Rebecca Anderson
*Assistant Examiner* — Karen Cheng
(74) *Attorney, Agent, or Firm* — Global IP Services; Tianhua Gu

(57) ABSTRACT

The invention relates to a novel important lycopene intermediate 3,7,11-trimethyl-1,3,6,10-tetraene-dodecyl diethyl phosphonate. A current lycopene intermediate 2,4,6,10-tetra-double bond pentadec-carbon phosphonate is difficult to synthesize. The invention provides a novel intermediate, which has the following synthesis steps of: preparing 2,6,10-trimethyl-3,5,9-undecane triene-1-aldehyde from pseudoionone; preparing 2,6,10-trimethyl-2,5,9-undecane triene-1-aldehyde from the 2,6,10-trimethyl-3,5,9-undecane triene-1-aldehyde; and subjecting the 2,6,10-trimethyl-2,5,9-undecane triene-1-aldehyde and tetraethyl methylenediphosphonate to condensation reaction to obtain target product. The invention can generate novel intermediate from raw material pseudoionone only by four reactions, thus the reactions are easy to control and great industrial value are achieved.

8 Claims, No Drawings

LYCOPENE INTERMEDIATE 1, 3, 6, 10-TETRA-DOUBLE BOND PENTADEC-CARBON PHOSPHONATE AS WELL AS PREPARATION METHOD AND USE THEREOF

CROSS REFERENCE TO RELATED PATENT APPLICATION

The present application is the US national stage of PCT/CN2011/071657 filed on Mar. 9, 2011, which claims the priority of the Chinese patent application No. 201010120583.3 filed on Mar. 9, 2010.

FIELD OF THE INVENTION

The invention relates to a novel important lycopene intermediate 3,7,11-trimethyl-1,3,6,10-tetraene-dodecyl diethyl phosphonate as well as a preparation method and use thereof

BACKGROUND OF THE INVENTION

In nature, there are approximately 600 types of carotenoids, but only six of them can be used for industrial production by manufacturers including Roche Company and BASF Company, and lycopene, as an important product, plays a key role in free radical removal, anti-aging, tumor inhibition, treatment for heart disease and the like and is widely applied to drugs, food additives and feed additives. Roche Company has developed a Wittig reaction-featured synthetic route in which expensive and toxic raw material triphenylphosphine is used, and triphenylphosphine is used in a variety of other early synthesis methods as well.

Babler J. H et al. reported a novel Wittig-Horner reaction-featured method for the synthesis of lycopene in WO 0031086, in which 3,7,11-trimethyl-2,4,6,10-tetraene-dodecyl diethyl phosphonate is used as key intermediate and condensed with decadialdehyde under the catalysis of base to prepare lycopene, and the synthesis steps are as follows:

At first, pseudoionone (2) reacts with acetylene anion to obtain tertiary alcohol (7) (i.e. 3,7,11-trimethyl-4,6,10-dodecyl triene-1-alkynyl-3-alcohol):

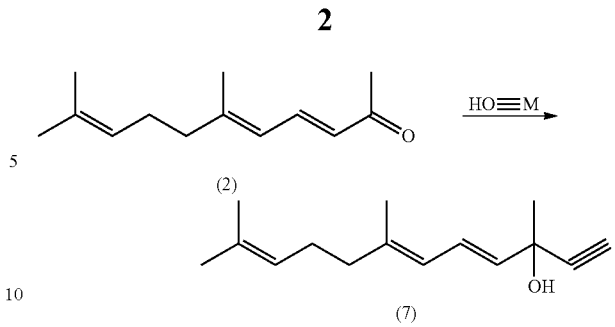

Then, the resultant tertiary alcohol (7) reacts with diethyl chlorophosphite to obtain propadiene pentadec-carbon phosphonate (6) (i.e. 3,7,11-trimethyl-1,2,4,6,10-pentaene-dodecyl diethyl phosphonate):

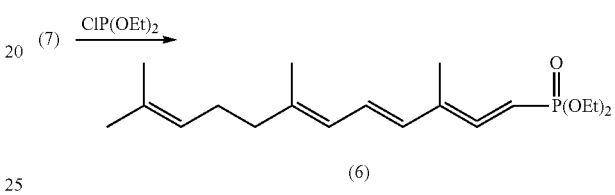

Afterwards, the propadiene pentadec-carbon phosphonate (6) is partially reduced and converted into pentadec-carbon phosphonate (5) (i.e. 3,7,11-trimethyl-2,4,6,10-tetraene-dodecyl diethyl phosphonate)

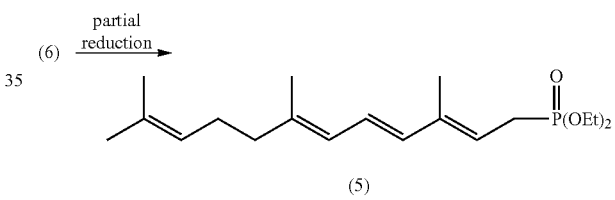

Finally, the pentadec-carbon phosphonate (5) and decadialdehyde (8) (i.e. 2,7-dimethyl-2,4,6-trieneoctane-1,8-dialdehyde) are condensed under the catalysis of base to prepare lycopene (1):

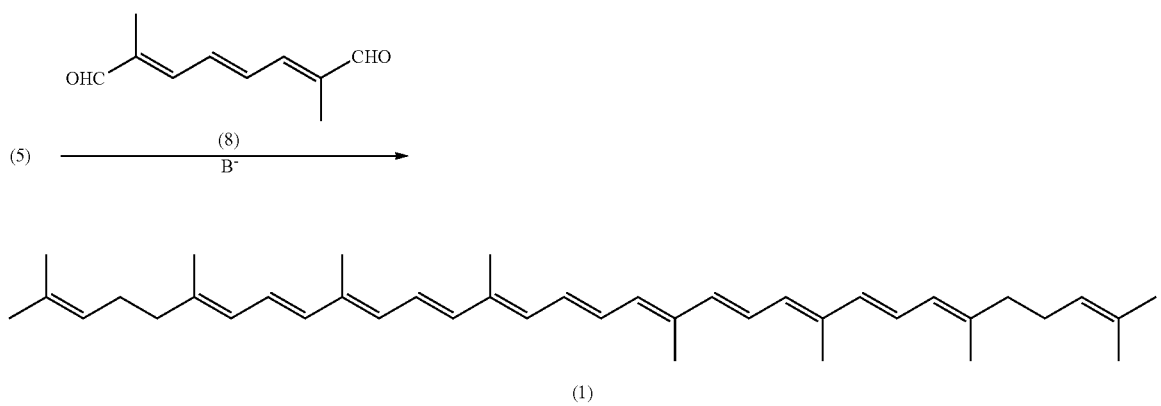

In the synthesis method above, the new compound 2,4,6,10-tetra-double bond pentadec-carbon phosphonate (5) is used as key intermediate, which avoids the use of triphenylphosphine; besides, with the pseudoionone as raw material, the target product lycopene can be obtained only by reactions in four steps, so the route is simple and convenient and tremendous progress is achieved compared with previous methods. However, this route has some problems: first, it is difficult, to a certain extent, to obtain propadiene pentadec-carbon phosphonate (6) by means of the reaction between tertiary alcohol (7) and diethyl chlorophosphite; second, it is difficult to grasp the reduction technology for selectively reducing propadiene pentadec-carbon phosphonate (6) into pentadec-carbon phosphonate (5).

SUMMARY OF THE INVENTION

The technical problem to be solved by the invention is to overcome the defects in the prior art, and provide a simple and convenient reaction route for preparing novel lycopene intermediate 1,3,6,10-tetra-double bond pentadec-carbon phosphonate (i.e. 3,7,11-trimethyl-1,3,6,10-tetraene-dodecyl diethyl phosphonate), and further preparing lycopene.

Therefore, the technical proposal below is adopted by the invention: a preparation method of 1,3,6,10-tetra-double bond pentadec-carbon phosphonate comprises the steps of:

1) pseudoionone (2) reacts with sulfonium chloride to obtain epoxide (9), and then ring opening is performed under catalysis to obtain 3-pos double bond C-14 aldehyde (3A), having a chemical name of 2,6,10-trimethyl-3,5,9-undecane triene-1-aldehyde and a structural formula below:

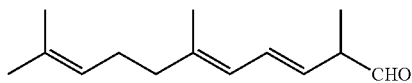

2) from the 3-pos double bond C-14 aldehyde (3A), 2-pos double bond C-14 aldehyde (3B) is prepared, having a chemical name of 2,6,10-trimethyl-2,5,9-undecane triene-1-aldehyde and a structural formula below:

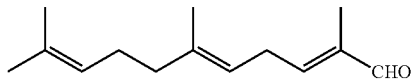

3) Then, the 2-pos double bond C-14 aldehyde (3B) and tetraethyl methylenediphosphonate are subjected to condensation reaction to obtain the target compound 1,3,6,10-tetra-double bond pentadec-carbon phosphonate (4), The synthetic route of the above steps is as follows:

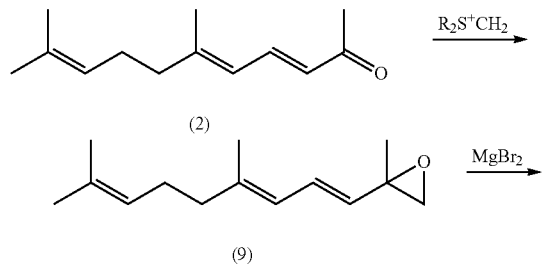

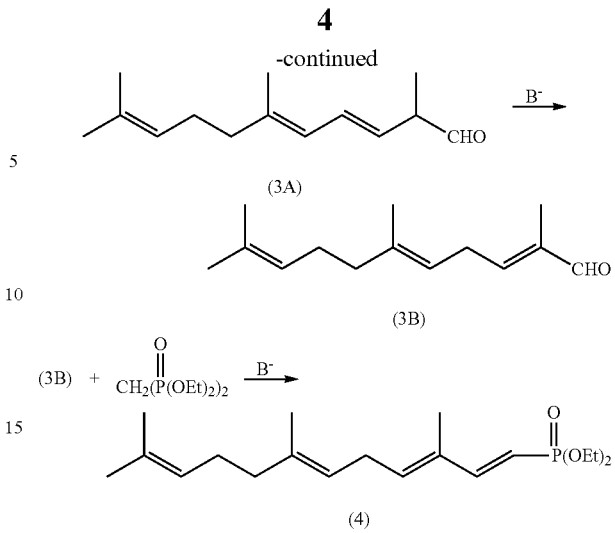

The reaction raw materials, pseudoionone and tetraethyl methylenediphosphonate, are staple industrial products.

The condensation reaction is performed under the presence of base that may be inorganic base, such as sodium hydride and potassium hydride, or that may be organic base, such as alkali metal salt of alcohols or lithium alkylide, strong bases like sodium alcoholate, sodium tert-butoxide, potassium tert-butoxide and butyl lithium are preferred, and other strong bases are not particularly restricted. The molar weight of base is 1.0-1.2 times as much as that of 2-pos double bond C-14 aldehyde (3B), preferably 1.02-1.1 times. The molar weight of tetraethyl methylenediphosphonate is 1.0-1.3 times as much as that of 2-pos double bond C-14 aldehyde (3B), preferably 1.05-1.15 times.

In the above condensation reaction, the reaction raw material tetraethyl methylenediphosphonate can firstly react with the base to obtain corresponding carbanions, and then the reaction raw material 2-pos double bond C-14 aldehyde (3B) is added for condensation reaction; or the etraethyl methylenediphosphonate and the 2-pos double bond C-14 aldehyde (3B) can be mixed together and then added dropwise into the base, both ways are beneficial for controlling the reaction better.

The temperature for the condensation reaction is 0-30° C., preferably 10-20° C.; and after the condensation reaction, water is added to reaction system in order to remove, by layering, the metal salt of the byproduct diethyl phosphate.

The condensation reaction is performed under the presence of organic solvent that is ether solvent or dipolar aprotic solvent, the ether solvent is ether, tetrahydrofuran or ethylene glycol dimethyl ether, and the dipolar aprotic solvent is dimethyl formamide (DMF), dimethyl sulfoxide (DMSO) or hexamethylphosphoric triamide (HMPTA).

As discussed above, the invention can obtain the target product 1,3,6,10-tetra-double bond pentadec-carbon phosphonate (4) from the raw material pseudoionone only by the reactions in four steps, so the invention has the advantages of simple and convenient process route, easily available raw materials, low cost and great industrial value.

The 1,3,6,10-tetra-double bond pentadec-carbon phosphonate (4) obtained above can be subjected to condensation reaction directly with decadialdehyde (8) in order to prepare lycopene (1), without the preparation of 2,4,6,10-tetra-double bond pentadec-carbon phosphonate (5), thus the reaction from 1,3,6,10-tetra-double bond pentadec-carbon phosphonate (4) to 2,4,6,10-tetra-double bond pentadec-carbon phosphonate (5) is omitted, and the synthetic route is as follows:

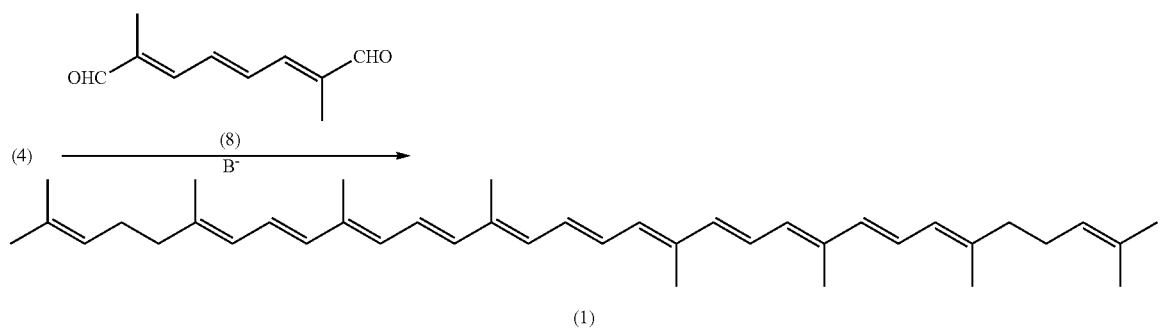

Before the condensation reaction, pentadec-carbon phosphonate is firstly subjected to sufficient rearrangement dissociation reaction by base so as to be completely changed into corresponding carbanions, and then 2,7-dimethyl-2,4,6-trieneoctane-1,8-dialdehyde compound is dropwise added to the solution in aprotic solvent for the purpose of condensation reaction. This way is beneficial for the change of the raw material 1,3,6,10-tetra-double bond pentadec-carbon phosphonate (4) into carbanions by means of sufficient rearrangement dissociation reaction, and is also beneficial for controlling the reaction better.

The rearrangement dissociation reaction and the condensation reaction above are performed under the presence of base that may be organic base, such as alkali metal salt of alcohols or lithium alkylide, strong bases like sodium alcoholate, sodium tert-butoxide, potassium tert-butoxide and butyl lithium are preferred, and other strong bases are not particularly restricted. The molar weight of base is 1.0-1.2 times as much as that of 1,3,6,10-tetra-double bond pentadec-carbon phosphonate (4), preferably 1.02-1.1 times. The molar weight of decadialdehyde (8) is 0.4-0.6 times as much as that of 1,3,6,10-tetra-double bond pentadec-carbon phosphonate (4).

The temperature for the rearrangement dissociation reaction and the condensation reaction is −40-30° C., preferably −20-10° C.; the reactions are performed under the presence of organic solvent that is ether solvent or dipolar aprotic solvent, the ether solvent is ether, tetrahydrofuran or ethylene glycol dimethyl ether, and the dipolar aprotic solvent is dimethyl formamide DMF, dimethyl sulfoxide DMSO or hexamethylphosphoric triamide HMPTA.

The invention, during the preparation of 2-pos double bond C-14 aldehyde (3B) from 3-pos double bond C-14 aldehyde (3A), specifically comprises the steps that: a) 2,6,10-trimethyl-3,5,9-undecane triene-1-aldehyde (both crude product and fine product are acceptable) reacts with aqueous solution of sodium bisulfite to obtain adduct sodium bisulfite salt, and excessive amount of the sodium bisulfite (both saturated concentration and other concentrations are acceptable) is used to guarantee smooth salt-forming reaction; b) layering is performed upon sufficient salt formation, an organic solvent is used for extracting an aqueous layer to remove residual organic impurities, and the product sodium bisulfite salt is contained in the aqueous layer for future use; c) the aqueous layer and the organic solvent are stirred together, sodium carbonate or base is added in batches for treatment, or the aqueous layer is firstly treated with sodium carbonate or base and then added with the organic solvent for extraction; the amount of the sodium carbonate or base is more than that of the sodium bisulfite in the step a) to guarantee the complete dissociation of sodium bisulfite salt; and d) layering is performed, and the resultant organic layer is water-rinsed and dried to obtain the fine product 2,6,10-trimethyl-2,5,9-undecane triene-1-aldehyde, i.e. 2-pos double bond C-14 aldehyde (3B).

Typically, preparation of adduct from aldehyde and sodium bisulfite and then hydrolysis is the common purification method for aldehydes, and in the invention, aldehyde, after being treated as discussed above, is not only purified, but also directly rearranged as the target product, and its mechanism is as follows:

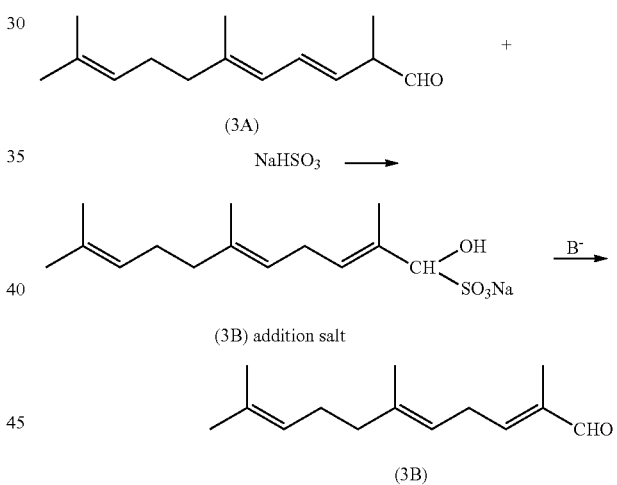

That is to say, double bond migration has occurred at the time of addition, and the driving force is the double bond migration caused by anion stabilization during the addition of aldehyde group and bisulfite. After such treatments, the rearranged target product 2-pos double bond C-14 aldehyde (3B) is obtained, and the purification effect is achieved; preferably, the crude product 3-pos double bond C-14 aldehyde (3A) is directly subjected to reaction, and the purity of product is quite high after the simple removal of solvent by evaporation, thus the reaction requirements in the next step can be met; however, the current common purification method has no purification effect, so rectification is indispensable.

As discussed above, the invention can obtain the target product lycopene from the raw material pseudoionone only by the reactions in five steps, so the invention has the advantages of simple and convenient process route, easily available raw materials, low cost and great industrial value.

Further description is made below to the invention with reference to the embodiments.

DETAILED DESCRIPTION OF THE INVENTION

The analysis instruments and equipment used in the embodiments are as follows: gas chromatography mass spectrometry MS5973N-GC6890N (Agilent Technologies); nuclear magnetic resonance instrument, AVANCE DMX 400M (TMS Internal Label); infrared spectrometer, NICOLET 360FT-IR; and gas chromatography, SHANGHAI TECHCOMP 7890F.

Embodiment 1

Preparation of 3-pos Double Bond C-14 Aldehyde (3A) (2,6,10-trimethyl-3,5,9-undecane triene-1-Aldehyde)

Reaction is performed according to the current method (see Embodiments 8 and 13 in U.S. Pat. No. 4,000,131). 20 g (0.5 mol) sodium hydride (60% content) is added to a 500 ml three-necked bottle under the protection of nitrogen, paraffin oil is removed by rinsing twice with 50 ml n-hexane each time; then, 160 ml dimethyl sulfoxide is added, oil bath is stirred magnetically and heated to an external temperature of 65° C., which is followed by reaction for 1 hour, a large amount of gas is discharged, and oil bath is cooled to room temperature after no gas is generated.

Another 1000 ml three-necked bottle under the protection of nitrogen is added with 102 g (0.5 mol) trimethyl iodinated sulfonium chloride and 300 ml mixture of dimethyl sulfoxide and tetrahydrofuran based on a ratio of 1:1 (volume ratio), mechanical stirring is performed, the sodium salt solution prepared above is dropwise added while ice salt bath is cooled, the temperature is maintained within a range from 0 to 5° C. while addition, and the addition can be finished about half an hour later; stirring is continued for 2 hours. 20 ml water is added upon complete reaction and stirred for 10 minutes, 200 ml n-hexane and 200 ml sodium hydride aqueous solution with the concentration of 10% are then added, layering is performed, organic layer is rinsed by 50 ml sodium hydride aqueous solution with the concentration of 10%, dried by magnesium sulfate and filtered, and the solvent is dried by evaporation under reduced pressure to obtain 35.2 g epoxide (9) crude product.

7.6 g 1,2-dibromoethane (0.04 mol) and 1.1 g magnesium powder (0.045 mol) are used for preparing magnesium bromide suspension in 50 ml ether, the suspension is put under the protection of nitrogen and magnetically stirred, 34.8 g epoxide (9) is dropwise added and dissolved in the solution of 100 ml ether while cold bath is maintained at the temperature of −10° C., the addition can be finished about 20 minutes later, stirring is continued for 5 minutes; 200 ml diluted reaction solution of ether and 200 ml sodium hydride aqueous solution with the concentration of 10% are added, layering is performed, organic layer is rinsed by 50 ml sodium hydride aqueous solution with the concentration of 10%, dried by magnesium sulfate and filtered, and the solvent is dried by evaporation under reduced pressure to obtain 30.2 g C-14 aldehyde (3A) crude product, which is a mixture consisting of 2R and 2S, 3-pos cis-trans isomer and 5-pos cis-trans isomer. The product has the content of 92.5% and the yield of 73.3% according to GC analysis.

Structural Confirmation of the Product:
GC-MS (m/e): 206, 191, 163, 135, 121, 109, 95 (100%), 69, 55, 41;
IR (v/cm$^{-1}$): 1672, 1612;

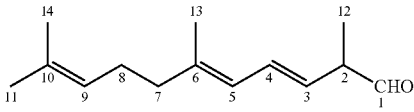

$^1$HNMR (δppm, 400 MHz, CDCl$_3$): 1.189-1.206 (m, 3H, C12-H), 1.427 (s, 3H, C14-H), 1.610 (s, 3H, C11-H), 1.687 (s, 3H, C13-H), 1.746-1.869 (m, 2H, C8-H), 2.092-2.134 (m, 2H, C7-H), 3.455-3.563 (m, 1H, C2-H), 5.092-5.101 (m, 1H, C9-H), 5.095-5.164 (m, 1H, C3-H), 6.058 (d, J=9.6 Hz, 1H, C5-H), 6.445 (t, J=9.6 Hz, 1H, C4-H), 9.537 (s, 1H, —CHO).

Embodiment 2

Preparation of 2-pos Double Bond C-14 aldehyde (3B) (2,6,10-trimethyl-2,5,9-undecane triene-1-aldehyde)

6.5 g C-14 aldehyde (3A) crude product prepared in the embodiment 1 and 6.5 g sodium bisulfate are added and dissolved in 40 ml aqueous solution, the solution is put under the protection of nitrogen and magnetically stirred for 20 minutes, and organic matters disappear basically; 30 ml cyclohexane is added for stirring for 5 minutes and layering is performed; aqueous layer is added with 60 ml cyclohexane, 7 g potassium carbonate is added under stirring, and after that, stirring is performed for 10 minutes and is followed by layering; organic layer is rinsed by 20 ml sodium hydride aqueous solution with the concentration of 10%, dried by magnesium sulfate and filtered, and the solvent is dried by evaporation under reduced pressure to obtain 5.5 g C-14 aldehyde (3B) crude product. The product has the content of 94.5% and the yield of 86.4% according to GC analysis.

Structural Confirmation of the Product:
GC-MS (m/e): 206, 191, 177, 163, 150, 135, 123, 109, 95, 81, 69 (100%), 53, 41, 29;

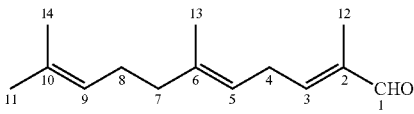

$^1$HNMR (δppm, 400 MHz, CDCl$_3$): 1.07 (t, J=7.2 Hz, 3H, C12-H), 1.17 (d, J=6.8 Hz, 3H, C13-H), 1.33 (t, J=6.8 Hz, 3H, C11-H, C14-H), 2.18-2.33 (m, 4H, C8-H, C7-H), 2.53-2.60 (m, 2H, C4-H), 5.09-5.11 (m, 1H, C9-H), 5.47-5.52 (m, 1H, C5-H), 6.52 (t, J=6.4 Hz, 1H, C3-H), 9.69 (s, 1H, —CHO).

Comparative Embodiment 1

Preparation (Current Method) of 2-pos Double Bond C-14 aldehyde (3B) (2,6,10-trimethyl-2,5,9-undecane triene-1-aldehyde)

6.5 g C-14 aldehyde (3A) crude product prepared in the embodiment 1 is dissolved in 15 ml methanol, the solution is put under the protection of nitrogen and added with 0.25 g potassium hydroxide under magnetic stirring, stirring is then continued for 35 minutes; 60 ml sodium hydride aqueous solution with the concentration of 10% and 60 ml cyclohexane are added, layering is performed, organic layer is rinsed by 30 ml sodium hydride aqueous solution with the concentration of 10%, dried by magnesium sulfate and filtered, and the solvent is dried by evaporation under reduced pressure to obtain 4.2 g C-14 aldehyde (3B) crude product. The product has the content of 85.5% and the yield of 59.8% according to GC analysis. The product's NMR spectroscopy is consistent with the embodiment 2.

Embodiment 3

Preparation of 2-pos Double Bond C-14 aldehyde (3B) (2,6,10-trimethyl-2,5,9-undecane triene-1-aldehyde)

6.5 g C-14 aldehyde (3A) crude product prepared in the embodiment 1 and 6.5 g sodium bisulfate are added and dissolved in 40 ml aqueous solution, the solution is put under the protection of nitrogen and magnetically stirred for 20 minutes, and organic matters disappear basically; 20 ml methylbenzene is added for stirring for 5 minutes and layering is performed; aqueous layer is added with 40 ml dichloromethane, 7 g potassium carbonate is added under stirring, and after that, stirring is performed for 10 minutes and is followed by layering; organic layer is rinsed by 20 ml sodium hydride aqueous solution with the concentration of 10%, dried by magnesium sulfate and filtered, and the solvent is dried by evaporation under reduced pressure to obtain 5.7 g C-14 aldehyde (3B) crude product. The product has the content of 93.5% and the yield of 88.6% according to GC analysis. The product's NMR spectroscopy is consistent with the embodiment 2.

Embodiment 4

Preparation of 1,3,6,10-tetra-Double Bond pentadec-carbon phosphonate (4) (3,7,11-trimethyl-1,3,6,10-tetraene-dodecyl diethyl phosphonate)

1.1 g (0.0275 mol) sodium hydride (60% content) is added to a 100 ml three-necked bottle under the protection of nitrogen, paraffin oil is removed by rinsing twice with 10 ml n-hexane each time; then, 10 ml methylbenzene is added, 8.6 g tetraethyl methylenediphosphonate (0.03 mol) is dropwise added to the solution of 20 ml methylbenzene under magnetic stirring, the temperature of cold water bath is maintained within a range from 10 to 15° C. while addition, a large amount of gas is discharged, the addition can be finished about half an hour later, and stirring is continued for reaction for half an hour; afterwards, 5.1 g C-14 aldehyde (3B) (prepared in the embodiment 2, 0.025 mol) is dropwise added and dissolved in the solution of 20 ml methylbenzene, the temperature of cold water bath is maintained within a range from 10 to 15° C. while addition, the addition can be finished about half an hour later, and stirring is continued for reaction for half an hour. 20 ml water is added to the reaction mixture solution, which is followed by stirring for 10 minutes and layering, organic layer is rinsed by 20 ml sodium hydride aqueous solution with the concentration of 10%, dried by magnesium sulfate and filtered, and the solvent is dried by evaporation under reduced pressure to obtain 7.5 g 1,3,6,10-tetra-double bond pentadec-carbon phosphonate (4) crude product, which is light brown liquid and has the gas phase content of 93.2% and the yield of 88.5%.

Structural Confirmation:

GC-MS (m/e): 340, 325, 284, 271, 243, 217 (100%), 205, 192, 159, 105, 79

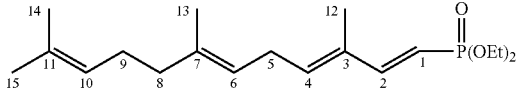

$^1$HNMR (δppm, 400 MHz, CDCl$_3$): 7.095 (dd, J=17.2 Hz, 4.8 Hz, 1H, C2-H), 6.643-6.699 (m, 1H, C4-H), 5.823 (t, J=4.8 Hz, 1H, C6-H), 5.605 (t, J=17.6 Hz, 1H, C1-H), 5.602-5.7141 (m, 1H, C10-H), 4.023-4.095 (m, 4H, O—C*H2-CH3), 2.614-2.729 (m, 1H, C5-H), 2.272-2.522 (m, 4H, C8-H and C9-H), 1.781 (s, 3H, C13-H), 1.686 (s, 3H, C14-H), 1.609 (s, 3H, C15-H), 1.313 (t, J=7.2 Hz, 6H, O—CH2-C*H3), 0.854 (d, J=6.8 Hz, 3H, C12-H)

$^{13}$CNMR (100 MHz, CDCl$_3$) δ(ppm): 152.84 (C2); 152.77 (C2); 138.92 (C4); 138.76 (C4); 137.04 (C7); 134.04 (C11); 133.80 (C3); 119.71 (C10); 116.96 (C6); 112.56 (C1); 110.65 (C1); 61.59, 61.55 (O—C*H2-CH3); 29.61 (C8); 24.36 (C9); 21.83 (C5); 21.80 (C15); 16.43 and 16.38 (O—CH2-C*H3); 14.05 (C14); 12.49 (C13); 11.84 (C12)

DEPT135: 152.84; 152.77; 138.92; 138.76; 119.71; 116.96; 112.56; 110.65; 61.59 (D); 61.55 (D); 29.61 (D); 24.36 (D); 21.83 (D); 21.80; 16.43, 16.38; 14.05; 12.49; 11.84.

Embodiment 5

Preparation of 1,3,6,10-tetra-Double Bond pentadec-carbon phosphonate (4) (3,7,11-trimethyl-1,3,6,10-tetraene-dodecyl diethyl phosphonate)

1.1 g (0.0275 mol) sodium hydride (60% content) is added to a 100 ml three-necked bottle under the protection of nitrogen, paraffin oil is removed by rinsing twice with 10 ml n-hexane each time; then, 10 ml methylbenzene is added, 8.6 g tetraethyl methylenediphosphonate (0.03 mol) is dropwise added to the solution of 20 ml methylbenzene under magnetic stirring, the temperature of cold water bath is maintained within a range from 10 to 15° C. while addition, a large amount of gas is discharged, the addition can be finished about half an hour later, and stirring is continued for reaction for half an hour; afterwards, 5.1 g C-14 aldehyde (3B) (prepared in the embodiment 3, 0.025 mol) is dropwise added and dissolved in the solution of 20 ml methylbenzene, the temperature of cold water bath is maintained within a range from 10 to 15° C. while addition, the addition can be finished about half an hour later, and stirring is continued for reaction for half an hour. 20 ml water is added to the reaction mixture solution, which is followed by stirring for 10 minutes and layering, organic layer is rinsed by 20 ml sodium hydride aqueous solution with the concentration of 10%, dried by magnesium sulfate and filtered, and the solvent is dried by evaporation under reduced pressure to obtain 7.3 g 1,3,6,10-tetra-double bond pentadec-carbon phosphonate (4) crude product, which is light brown liquid and has the gas phase content of 93.5% and the yield of 86.1%. The product's NMR spectroscopy is consistent with the embodiment 4.

Embodiment 6

Preparation of Lycopene from 1,3,6,10-tetra-Double Bond pentadec-carbon phosphonate (4)

6.8 g (0.02 mol) 1,3,6,10-tetra-double bond pentadec-carbon phosphonate (4) prepared in the embodiment 5 and 30 ml mixture of tetrahydrofuran and dimethyl sulfoxide based on a ratio of 8:1 (volume ratio) are added to a 250 ml three-necked bottle under the protection of nitrogen, 2.3 g (0.021 mol) potassium tert-butoxide is added at about 5° C. (ice water bath) under mechanical stirring, stirring is performed for 2 hours while the temperature is maintained, then 1.6 g decadialdehyde (8) (0.0098 mol) is dropwise added to 10 ml mixture of tetrahydrofuran and dimethyl sulfoxide based on a ratio of 8:1 (volume ratio) (For the preparation of 8, see Embodiment XIV in U.S. Pat. No. 5,061,819), the addition can be finished about 20 minutes later, stirring is continued for 15 minutes while the temperature is maintained, and the temperature then rises to a range from 20-25° C. for reaction for 1 hour. Addition of 100 ml chloroform upon complete reaction is followed by rinsing three times with sodium hydride aqueous solution with the concentration of 10% (75 ml each time), organic layer is dried by magnesium sulfate and filtered, the filtrate is dried by evaporation under reduced pressure to obtain crude product, and the crude product is re-crystallized with 30 ml methylene dichloride to obtain 2.8 g (the yield is 52.3%) product.

Structural Confirmation:

to obtain 29.8 g crude product. The product has the content of 91.8% according to GC analysis. Then, 30 g sodium bisulfate is added to the crude product and they are dissolved in 200 ml aqueous solution, the solution is put under the protection of nitrogen and magnetically stirred for 20 minutes, and organic matters disappear basically; 60 ml methylbenzene is added for stirring for 5 minutes and layering is performed; aqueous layer is added with 100 ml methylene dichloride, 35 g potassium carbonate is added under stirring, and after that, stirring is performed for 10 minutes and is followed by layering; organic layer is rinsed by 20 ml sodium hydride aqueous solution with the concentration of 10%, dried by magnesium sulfate and filtered, and the solvent is dried by evaporation under reduced pressure to obtain 27.5 g C-14 aldehyde (3B). The product has the content of 93.5% according to GC analysis. The product's NMR spectroscopy is consistent with the embodiment 2.

Embodiments 8-13

Preparation of 1,3,6,10-tetra-Double Bond pentadec-carbon phosphonate (4) (3,7,11-trimethyl-1,3,6,10-tetraene-dodecyl diethyl phosphonate) Under Different Base, Solvent and Temperature Conditions A fixed amount of base and certain solvent (see the table below for the type of base and solvent) are added to a 100 ml three-necked bottle under the protection of nitrogen, 10 ml solvent (the same as the above solvent) with a fixed amount of

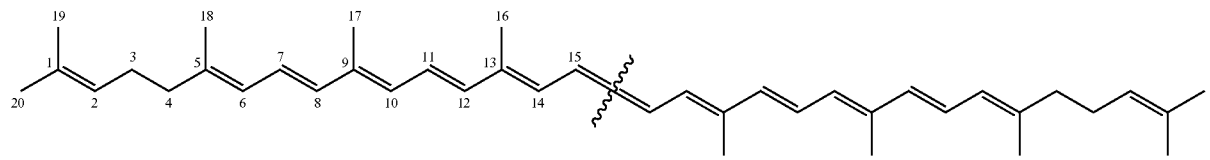

$^1$HNMR (δppm, 400 MHz, CDCl$_3$): δ 5.111, 5.975-6.943 (m, 8H, double bond H), 5.11 (m, 1H), 1.552 (S, 6H), 1.616 (S, 3H), 1.689 (S, 3H), 2.129 (S, 3H), 1.427-2.212 (m, 4H)

$^{13}$CNMR (100 MHz, CDCl$_3$) δ(ppm): 139.52 (C5); 137.37 (C12); 136.56 (C13); 136.19 (C9); 135.42 (C10); 132.66 (C14); 131.76 (C1); 131.58 (C8); 130.09 (C15); 125.73 (C11); 125.17 (C2); 124.82 (C6); 123.96 (C7); 40.25 (C4); 26.69 (C3); 25.72 (C20); 18.42 (C19); 16.97 (C18); 12.91 (C17); 12.81 (C16)

There are 13 peaks between δ(ppm) 120 and δ(ppm) 140; there are 7 peaks between δ(ppm) 10 and δ(ppm) 45, thus determining the all-trans structure and high purity of product.

DEPT135: 137.37; 135.42; 132.66; 131.58; 130.09; 125.73; 125.17; 124.82; 123.96; 58.48 (D); 40.25 (D); 26.69 (D); 25.72; 18.42; 16.97; 12.91; 12.81

Embodiment 7

Preparation of 2-pos Double Bond C-14 aldehyde (3B) (2,6,10-trimethyl-2,5,9-undecane triene-1-aldehyde)

C-14 aldehyde (3A) is prepared according to conditions and proportions that are totally the same as the embodiment 1 tetraethyl methylenediphosphonate (see the table below for molar weight) dissolved therein is dropwise added on the condition that magnetic stirring is performed and cold water bath is maintained within a range from 10 to 15° C., gas is discharged, the addition can be finished about half an hour later, and stirring is continued for reaction for 20 minutes. Then, 10 ml solvent (the same as the above solvent), with 2.1 g C-14 aldehyde having a formula (3B) (prepared in the embodiment 7, 0.010 mol) dissolved therein, is dropwise added on the condition that cold water bath is maintained at a particular temperature, the addition can be finished about half an hour later, and stirring is continued while the temperature is maintained for reaction for 20 minutes. 10 ml water and 20 ml ether are added to the reaction mixture solution, which is followed by stirring for 10 minutes and layering, organic layer is rinsed by 20 ml sodium hydride aqueous solution with the concentration of 10%, dried by magnesium sulfate and filtered, the solvent is dried by evaporation under reduced pressure to obtain 3,7,11-trimethyl-1,3,6,10-tetraene-dodecyl diethyl phosphonate crude product, which is light brown liquid. Measurement for gas phase content and calculation for yield are carried out, and the results are shown in the table below.

TABLE 1 sodium hydride and methylbenzene are replaced by different bases and different solvents and the amount of base is adjusted, the results are shown in the table below: (note: alkali metal alkoxide is sodium methoxide or sodium ethoxide, etc., and n-butyl lithium is 2.5 mol/l n-hexane solution)

| Embodiment | Type of Base | Amount of Base (Mol) | Solvent | Amount of Tetraethyl Methylene-diphosphonate (Mol) | Reaction Temperature (°C.) | Amount of Obtained Product (g) and Product Content (%) | Yield (%) |
|---|---|---|---|---|---|---|---|
| 8 | sodium ethoxide | 0.0120 | methyl-benzene | 0.0130 | 5 | 3.0; 93.1 | 87.6 |
| 9 | sodium tert-butoxide | 0.0100 | ethylene glycol dimethyl ether | 0.0100 | 10 | 3.1; 92.4 | 84.5 |
| 10 | potassium tert-butoxide | 0.0102 | dimethyl formamide | 0.0105 | 20 | 3.2; 93.2 | 87.7 |
| 11 | n-butyl lithium | 0.0120 | tetra-hydrofuran/n-hexane | 0.0130 | 0 | 3.3; 93.5 | 90.8 |
| 12 | dimethyl sulfoxide sodium salt | 0.0105 | dimethyl sulfoxide | 0.0108 | 30 | 3.0; 91.3 | 80.6 |
| 13 | sodium methoxide | 0.0110 | ether | 0.0115 | 15 | 1.7; 89.7 | 44.8 |

The obtained 1,3,6,10-tetra-double bond pentadec-carbon diethyl phosphonates are combined to obtain 17.3 g crude product for subsequent reactions, and the mixed crude product's NMR spectroscopy is consistent with the embodiment 4.

Embodiments 14-18

Preparation of Lycopene from 3,7,11-trimethyl-1,3,6,10-tetraene-dodecyl diethyl phosphonate under Different Base, Solvent and Temperature Conditions The crude products prepared in the embodiments 8-13 are used for future preparation of lycopene, and a series of condition experiments are carried out under different bases and solvents and at different temperatures. The specific process is as follows:

3.4 g (0.01 mol) 3,7,11-trimethyl-1,3,6,10-tetraene-dodecyl diethyl phosphonate crude product and 20 ml certain solvent are added to a 100 ml three-necked bottle under the protection of nitrogen, a fixed amount of base (see the table below for the type of base and solvent) is added at a particular temperature under mechanical stirring, stirring is performed for 2 hours while the temperature is maintained, then 10 ml solvent (the same as the above solvent) with a fixed amount of decadialdehyde having a formula (8) dissolved therein is dropwise added at a particular temperature (the same as the temperature for rearrangement dissociation), the addition can be finished about 20 minutes later, stirring is continued for 15 minutes while the temperature is maintained, and the temperature rises to a range from 25-30° C. for reaction for 1 hour. Addition of 100 ml chloroform upon complete reaction is followed by rinsing three times with sodium hydride aqueous solution with the concentration of 5% (75 ml each time), organic layer is dried by magnesium sulfate and filtered, the filtrate is dried by evaporation under reduced pressure to obtain lycopene crude product, and the lycopene crude product is re-crystallized with 30 ml methylene dichloride to obtain a fixed amount of lycopene product. The yield is calculated and the results are shown in the table below.

TABLE 2

The operation process is the same as the embodiment 6, but different bases, solvent and temperatures are adopted and the amount of base and decadialdehyde is adjusted.

| Embodiment | Type of Base | Amount of Base (Mol) | Solvent | Amount of Tetraethyl Decadialde-hyde (Mol) | Reaction Temperature (°C.) | Amount of Obtained Product (g) | Yield (%) |
|---|---|---|---|---|---|---|---|
| 14 | sodium ethoxide | 0.0120 | ether | 0.006 | −5 | 1.0 | 37.4 |
| 15 | sodium tert-butoxide | 0.0102 | ethylene glycol dimethyl ether | 0.005 | 10 | 1.4 | 52.4 |
| 16 | potassium tert-butoxide | 0.0105 | dimethyl formamide | 0.0045 | −20 | 1.7 | 63.5 |
| 17 | potassium tert-butoxide | 0.0105 | hexamethyl phosphoric triamide | 0.0040 | −30 | 1.6 | 59.8 |

TABLE 2-continued

The operation process is the same as the embodiment 6, but different bases, solvent and temperatures are adopted and the amount of base and decadialdehyde is adjusted.

| Embodiment | Type of Base | Amount of Base (Mol) | Solvent | Amount of Tetraethyl Decadialdehyde (Mol) | Reaction Temperature (° C.) | Amount of Obtained Product (g) | Yield (%) |
|---|---|---|---|---|---|---|---|
| 18 | n-butyl lithium | 0.0110 | tetrahydrofuran/ n-hexane | 0.0055 | −40 | 1.9 | 71.0 |

Note:
n-butyl lithium is 2.5 mol/l n-hexane solution

The nuclear magnetic spectrograms of the above products are consistent with the embodiment 6.

It needs to be noted that the contents and the embodiments in the invention are intended to demonstrate the practical applications of the technical proposal provided by the invention, and shall not be contemplated as limitations to the scope of the invention. Various modifications, equivalent substitutions or improvements can be made by those skilled in this art within the spirit and principle of the invention. The scope of the invention is defined by the appended claims.

What is claimed is:

1. A lycopene intermediate 1,3,6,10-tetra-double bond pentadec-carbon phosphonate, having a chemical name of 3,7,11-trimethyl-1,3,6,10-tetraene-dodecyl diethyl phosphonate and a structural formula as below:

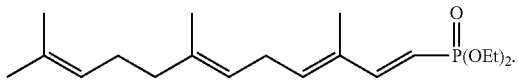

2. A preparation method of 1,3,6,10-tetra-double bond pentadec-carbon phosphonate of claim 1, comprising the steps of:
 1) Preparing 2,6,10-trimethyl-3,5,9-undecane triene-1-aldehyde from pseudoionone;
 2) Preparing 2,6,10-trimethyl-2,5,9-undecane triene-1-aldehyde from the 2,6,10-trimethyl-3,5,9-undecane triene-1-aldehyde obtained from the step 1); and
 3) Subjecting the 2,6,10-trimethyl-2,5,9-undecane triene-1-aldehyde and tetraethyl methylenediphosphonate to Wittig-Horner condensation reaction to obtain the 1,3,6,10-tetra-double bond pentadec-carbon phosphonate.

3. The preparation method of 1,3,6,10-tetra-double bond pentadec-carbon phosphonate according to claim 2, characterized in that the step 2) specifically comprises the steps of:
 a) reacting of 2,6,10-trimethyl-3,5,9-undecane triene-1-aldehyde with aqueous solution of sodium bisulfite to obtain aqueous solution of adduct sodium bisulfite salt, and in the reacting process excessive amount of the sodium bisulfite is used to create smooth salt-forming reaction;
 b) layering the aqueous solution of adduct sodium bisulfite salt obtained from step a) upon sufficient amount of the sodium bisulfite salt being formed, adding organic solvent to extract an aqueous layer for removing residual organic impurities, the extracted aqueous layer contains the adduct sodium bisulfite salt;
 c) adding organic solvent into the extracted aqueous layer containing adduct sodium bisulfite obtained from the step b) and stirring them together, adding sodium carbonate in batches for treatment, the amount of the sodium carbonate is more than that of the sodium bisulfite in the step a) to guarantee the complete dissociation of adduct sodium bisulfite salt; and
 d) layering the aqueous solution and organic layer obtained from step c) to obtain the organic layer containing the 2,6,10-trimethyl-2,5,9-undecane triene-1-aldehyde, then the organic layer is rinsed with water, dried, and the solvent removed by evaporation to obtain the 2,6,10-trimethyl-2,5,9-undecane triene-1-aldehyde.

4. The preparation method of 1,3,6,10-tetra-double bond pentadec-carbon phosphonate according to claim 3, characterized in that the temperature for salt formation and dissociation reaction is 10-40° C., and the organic solvent used is methylene dichloride, cyclohexane or methylbenzene.

5. The preparation method of 1,3,6,10-tetra-double bond pentadec-carbon phosphonate according to claim 2, characterized in that the temperature for condensation reaction is 0-30° C.

6. The preparation method of 1,3,6,10-tetra-double bond pentadec-carbon phosphonate according to claim 2, characterized in that the condensation reaction is performed under the presence of base and organic solvent.

7. The preparation method of 1,3,6,10-tetra-double bond pentadec-carbon phosphonate according to claim 6, characterized in that the base is inorganic base or organic base; the organic solvent is ether, tetrahydrofuran, ethylene glycol dimethyl ether, dimethyl formamide, dimethyl sulfoxide or hexamethylphosphoric triamide.

8. The preparation method of 1,3,6,10-tetra-double bond pentadec-carbon phosphonate according to claim 7, characterized in that water is added to reaction system after condensation reaction.

* * * * *